US007465319B2

(12) United States Patent
Tornier

(10) Patent No.: US 7,465,319 B2
(45) Date of Patent: Dec. 16, 2008

(54) SHOULDER OR HIP PROSTHESIS AND PROCESS FOR FITTING SAME

(75) Inventor: Alain Tornier, Saint Ismier (FR)

(73) Assignee: Tornier SAS, Saint Ismier (FR)

( * ) Notice: Subject to any disclaimer, the term of this patent is extended or adjusted under 35 U.S.C. 154(b) by 511 days.

(21) Appl. No.: 11/011,775

(22) Filed: Dec. 15, 2004

(65) Prior Publication Data
US 2005/0165490 A1 Jul. 28, 2005

(30) Foreign Application Priority Data
Dec. 19, 2003 (FR) .................................. 03 15069

(51) Int. Cl.
*A61F 2/40* (2006.01)
*A61F 2/38* (2006.01)

(52) U.S. Cl. ................ 623/19.11; 623/20.35

(58) Field of Classification Search ... 623/19.11–19.14, 623/22.11–22.2, 20.22, 20.35, 20.36
See application file for complete search history.

(56) References Cited

U.S. PATENT DOCUMENTS

| 3,694,820 | A |   | 10/1972 | Scales et al. |
|---|---|---|---|---|
| 3,815,157 | A |   | 6/1974  | Skorecki et al. |
| 3,842,442 | A |   | 10/1974 | Kolbel |
| 3,864,758 | A | * | 2/1975  | Yakich ..................... 623/22.13 |
| 3,869,730 | A | * | 3/1975  | Skobel ..................... 623/19.12 |
| 3,916,451 | A |   | 11/1975 | Buechel et al. |
| 3,978,528 | A |   | 9/1976  | Crep |
| 3,979,778 | A |   | 9/1976  | Stroot |
| 3,992,726 | A |   | 11/1976 | Freeman et al. |
| 4,003,095 | A |   | 1/1977  | Gristina |
| 4,030,143 | A |   | 6/1977  | Elloy et al. |
| 4,040,131 | A |   | 8/1977  | Gristina |
| 4,054,955 | A |   | 10/1977 | Seppo |
| 4,135,517 | A |   | 1/1979  | Reale |
| 4,179,758 | A |   | 12/1979 | Gristina |
| 4,206,517 | A |   | 6/1980  | Pappas et al. |
| 4,261,062 | A |   | 4/1981  | Amstutz et al. |

(Continued)

FOREIGN PATENT DOCUMENTS

CH            426096        12/1966

(Continued)

OTHER PUBLICATIONS

Rochetin, U.S. Appl. No. 11/194,452, entitled "Patellar Retractor and Method of Surgical Procedure on Knee," filed Aug. 2, 2005.

(Continued)

*Primary Examiner*—William H. Matthews
*Assistant Examiner*—Ann Schillinger
(74) *Attorney, Agent, or Firm*—Faegre & Benson LLP

(57) ABSTRACT

This prosthesis comprises a humeral or femoral component and an intermediate component. The concave surface of articulation of the humeral or femoral component is formed by a plate connected by a neck to a part of this component adapted to be anchored in the humeral or femoral medullary cavity. The intermediate component is provided with a member for retaining the humeral or femoral component in a position where the plate is in abutment against the first convex surface of the intermediate component. The retaining member defines a non-circular passage in which the neck is adapted to be displaced as a function of the movements of the humeral or femoral component with respect to the other components of the prosthesis. The retaining member defines with the first convex surface of articulation of the intermediate component a volume for receiving a part of the plate projecting radially with respect to the neck.

16 Claims, 6 Drawing Sheets

U.S. PATENT DOCUMENTS

| | | |
|---|---|---|
| 4,550,450 A | 11/1985 | Kinnett |
| 4,693,723 A | 9/1987 | Gabard |
| 4,822,370 A | 4/1989 | Schelhas |
| 4,846,840 A | 7/1989 | Leclercq et al. |
| 4,865,605 A | 9/1989 | Dines et al. |
| 4,865,609 A | 9/1989 | Roche |
| 4,892,549 A | 1/1990 | Figgie, III et al. |
| 4,919,670 A | 4/1990 | Dale et al. |
| 4,957,510 A | 9/1990 | Cremascoli |
| 4,963,155 A | 10/1990 | Lazerri et al. |
| 5,032,132 A | 7/1991 | Matsen, III et al. |
| 5,080,673 A | 1/1992 | Burkhead et al. |
| 5,080,685 A | 1/1992 | Bolesky et al. |
| 5,127,920 A | 7/1992 | MacArthur |
| 5,135,529 A | 8/1992 | Paxson et al. |
| 5,163,961 A | 11/1992 | Harwin |
| 5,171,289 A | 12/1992 | Tornier |
| 5,181,928 A | 1/1993 | Bolesky et al. |
| 5,192,329 A | 3/1993 | Christie et al. |
| 5,201,882 A | 4/1993 | Paxson |
| 5,206,925 A | 4/1993 | Nakazawa et al. |
| 5,222,984 A | 6/1993 | Forte |
| 5,261,914 A | 11/1993 | Warren |
| 5,314,479 A | 5/1994 | Rockwood, Jr. et al. |
| 5,314,485 A | 5/1994 | Judet |
| 5,314,487 A | 5/1994 | Schryver et al. |
| 5,326,359 A | 7/1994 | Oudard |
| 5,330,531 A | 7/1994 | Cappana |
| 5,358,526 A | 10/1994 | Tornier |
| 5,383,936 A | 1/1995 | Kubein-Meesenburg et al. |
| 5,405,399 A | 4/1995 | Tornier |
| 5,425,779 A | 6/1995 | Schlosser |
| 5,429,639 A | 7/1995 | Judet |
| 5,443,519 A | 8/1995 | Averill et al. |
| 5,458,650 A | 10/1995 | Carrett et al. |
| 5,462,563 A | 10/1995 | Shearer et al. |
| 5,505,731 A | 4/1996 | Tornier |
| 5,507,817 A | 4/1996 | Craig et al. |
| 5,507,818 A | 4/1996 | McLaughlin |
| 5,507,824 A | 4/1996 | Lennox |
| 5,549,682 A | 8/1996 | Roy |
| 5,580,352 A | 12/1996 | Sekel |
| 5,591,168 A | 1/1997 | Judet et al. |
| 5,662,651 A | 9/1997 | Tornier et al. |
| 5,676,702 A | 10/1997 | Ratron |
| 5,702,447 A | 12/1997 | Walch et al. |
| 5,702,457 A | 12/1997 | Walch et al. |
| 5,702,478 A | 12/1997 | Tornier |
| 5,702,486 A | 12/1997 | Craig et al. |
| 5,723,018 A | 3/1998 | Cyprien et al. |
| 5,728,161 A | 3/1998 | Camino et al. |
| 5,741,335 A | 4/1998 | Gerber et al. |
| 5,755,807 A * | 5/1998 | Anstaett et al. ............ 623/22.2 |
| 5,766,256 A | 6/1998 | Oudard et al. |
| 5,800,551 A | 9/1998 | Williamson et al. |
| 5,824,106 A | 10/1998 | Fournol |
| 5,879,395 A | 3/1999 | Tornier et al. |
| 5,879,405 A | 3/1999 | Ries et al. |
| 5,902,340 A | 5/1999 | White et al. |
| 5,910,171 A | 6/1999 | Kummer et al. |
| 5,928,285 A | 7/1999 | Bigliani |
| 5,944,758 A | 8/1999 | Mansat et al. |
| 5,961,555 A | 10/1999 | Huebner |
| 5,984,927 A | 11/1999 | Wenstrom, Jr. et al. |
| 6,015,437 A | 1/2000 | Stossel |
| 6,033,439 A | 3/2000 | Camino et al. |
| 6,045,582 A | 4/2000 | Prybyla |
| 6,045,583 A | 4/2000 | Gross et al. |
| 6,102,953 A | 8/2000 | Huebner |
| 6,129,764 A | 10/2000 | Servfidio |
| 6,162,254 A | 12/2000 | Timoteo |
| 6,165,224 A | 12/2000 | Tornier |
| 6,168,629 B1 | 1/2001 | Timoteo |
| 6,171,341 B1 | 1/2001 | Boileau et al. |
| 6,183,519 B1 | 2/2001 | Bonnin et al. |
| 6,197,062 B1 | 3/2001 | Fenlin |
| 6,197,063 B1 | 3/2001 | Dews |
| 6,203,575 B1 | 3/2001 | Farey |
| 6,206,925 B1 | 3/2001 | Tornier |
| 6,228,120 B1 | 5/2001 | Leonard et al. |
| 6,267,767 B1 | 7/2001 | Stroble et al. |
| 6,283,999 B1 | 9/2001 | Rockwood, Jr. |
| 6,299,646 B1 | 10/2001 | Chambat et al. |
| 6,312,467 B1 | 11/2001 | McGee |
| 6,328,758 B1 | 12/2001 | Tornier et al. |
| 6,334,874 B1 | 1/2002 | Tornier et al. |
| 6,364,910 B1 | 4/2002 | Shultz et al. |
| 6,368,352 B1 | 4/2002 | Camino et al. |
| 6,368,353 B1 | 4/2002 | Arcand |
| 6,379,387 B1 | 4/2002 | Tornier |
| 6,398,812 B1 | 6/2002 | Masini |
| 6,406,495 B1 | 6/2002 | Schoch |
| 6,406,496 B1 | 6/2002 | Rüter |
| 6,436,144 B1 | 8/2002 | Ahrens |
| 6,436,147 B1 | 8/2002 | Zweymuller |
| 6,454,809 B1 | 9/2002 | Tornier |
| 6,458,136 B1 | 10/2002 | Allard et al. |
| 6,475,243 B1 | 11/2002 | Sheldon et al. |
| 6,488,712 B1 | 12/2002 | Tornier et al. |
| 6,494,913 B1 | 12/2002 | Huebner |
| 6,506,214 B1 | 1/2003 | Gross |
| 6,508,840 B1 | 1/2003 | Rockwood, Jr. et al. |
| 6,514,287 B2 | 2/2003 | Ondrla et al. |
| 6,520,994 B2 | 2/2003 | Nogarin |
| 6,530,957 B1 | 3/2003 | Jack |
| 6,540,770 B1 | 4/2003 | Tornier et al. |
| 6,558,425 B2 | 5/2003 | Rockwood |
| 6,569,202 B2 | 5/2003 | Whiteside |
| 6,582,469 B1 | 6/2003 | Tornier |
| 6,589,281 B2 | 7/2003 | Hyde, Jr. |
| 6,599,295 B1 | 7/2003 | Tornier et al. |
| 6,620,197 B2 | 9/2003 | Maroney et al. |
| 6,626,946 B1 | 9/2003 | Walch et al. |
| 6,673,114 B2 | 1/2004 | Hartdegen et al. |
| 6,673,115 B2 | 1/2004 | Resch et al. |
| 6,679,916 B1 | 1/2004 | Frankle et al. |
| 6,736,851 B2 | 5/2004 | Maroney et al. |
| 6,746,487 B2 | 6/2004 | Scifert et al. |
| 6,749,637 B1 | 6/2004 | Bahler |
| 6,755,866 B2 | 6/2004 | Southworth |
| 6,761,740 B2 | 7/2004 | Tornier |
| 6,767,368 B2 | 7/2004 | Tornier |
| 6,780,190 B2 | 8/2004 | Maroney |
| 6,783,549 B1 | 8/2004 | Stone et al. |
| 6,790,234 B1 | 9/2004 | Frankle |
| 6,802,864 B2 | 10/2004 | Tornier |
| 6,824,567 B2 | 11/2004 | Tornier et al. |
| 6,863,690 B2 | 3/2005 | Ball et al. |
| 6,875,234 B2 | 4/2005 | Lipman et al. |
| 6,887,277 B2 | 5/2005 | Rauscher et al. |
| 6,890,357 B2 | 5/2005 | Tornier |
| 6,890,358 B2 | 5/2005 | Ball et al. |
| 6,942,699 B2 | 9/2005 | Stone et al. |
| 6,953,478 B2 | 10/2005 | Bouttens et al. |
| 6,969,406 B2 | 11/2005 | Tornier |
| 7,011,686 B2 | 3/2006 | Ball et al. |
| 7,033,396 B2 | 4/2006 | Tornier |
| 7,066,959 B2 | 6/2006 | Errico |
| 7,108,719 B2 | 9/2006 | Horber |
| 7,166,132 B2 | 1/2007 | Callaway et al. |
| 7,169,184 B2 | 1/2007 | Dalla Pria |
| 7,175,663 B1 | 2/2007 | Stone |
| 7,195,645 B2 | 3/2007 | Disilvestro et al. |
| 7,238,207 B2 | 7/2007 | Blatter et al. |

| | | |
|---|---|---|
| 7,238,208 B2 | 7/2007 | Camino et al. |
| 7,297,163 B2 | 11/2007 | Huebner |
| 7,309,360 B2 | 12/2007 | Tornier et al. |
| 7,329,284 B2 | 2/2008 | Maroney et al. |
| 7,338,498 B2 | 3/2008 | Long et al. |
| 7,338,528 B2 | 3/2008 | Stone et al. |
| 2001/0032021 A1 | 10/2001 | McKinnon |
| 2001/0047210 A1 | 11/2001 | Wolf |
| 2001/0049561 A1 | 12/2001 | Dews et al. |
| 2002/0032484 A1 | 3/2002 | Hyde, Jr. |
| 2002/0099381 A1 | 7/2002 | Maroney |
| 2002/0138148 A1 | 9/2002 | Hyde, Jr. |
| 2002/0143402 A1 | 10/2002 | Steinberg |
| 2002/0151982 A1 | 10/2002 | Masini |
| 2003/0009170 A1 | 1/2003 | Tornier |
| 2003/0009171 A1 | 1/2003 | Tornier |
| 2003/0028198 A1 | 2/2003 | Tornier et al. |
| 2003/0074072 A1 | 4/2003 | Errico et al. |
| 2003/0097183 A1 | 5/2003 | Rauscher et al. |
| 2003/0114933 A1 | 6/2003 | Bouttens et al. |
| 2003/0149485 A1 | 8/2003 | Tornier |
| 2003/0158605 A1 | 8/2003 | Tornier |
| 2004/0002765 A1 | 1/2004 | Maroney et al. |
| 2004/0006392 A1 | 1/2004 | Grusin et al. |
| 2004/0030394 A1 | 2/2004 | Horber |
| 2004/0034431 A1 | 2/2004 | Maroney et al. |
| 2004/0039449 A1 | 2/2004 | Tornier |
| 2004/0064189 A1 | 4/2004 | Maroney et al. |
| 2004/0064190 A1 | 4/2004 | Ball et al. |
| 2004/0133276 A1 | 7/2004 | Lang et al. |
| 2004/0134821 A1 | 7/2004 | Tornier |
| 2004/0138754 A1 | 7/2004 | Lang et al. |
| 2004/0148033 A1 | 7/2004 | Schroeder |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0210220 A1 | 10/2004 | Tornier |
| 2004/0210317 A1 | 10/2004 | Maroney et al. |
| 2004/0215200 A1 | 10/2004 | Tornier et al. |
| 2004/0220673 A1 | 11/2004 | Pria |
| 2004/0220674 A1 | 11/2004 | Pria |
| 2004/0225367 A1 | 11/2004 | Glien et al. |
| 2004/0230197 A1 | 11/2004 | Tornier et al. |
| 2004/0267370 A1 | 12/2004 | Ondria |
| 2005/0008672 A1 | 1/2005 | Winterbottom et al. |
| 2005/0015154 A1 | 1/2005 | Lindsey et al. |
| 2005/0043805 A1 | 2/2005 | Chudik |
| 2005/0049709 A1 | 3/2005 | Tornier |
| 2005/0055102 A1 | 3/2005 | Tornier et al. |
| 2005/0065612 A1 | 3/2005 | Winslow |
| 2005/0085919 A1 | 4/2005 | Durand-Allen et al. |
| 2005/0085921 A1 | 4/2005 | Gupta et al. |
| 2005/0090902 A1 | 4/2005 | Masini |
| 2005/0107882 A1 | 5/2005 | Stone et al. |
| 2005/0113931 A1 | 5/2005 | Horber |
| 2005/0119531 A1 | 6/2005 | Sharratt |
| 2005/0143829 A1 | 6/2005 | Ondria et al. |
| 2005/0165490 A1 | 7/2005 | Tornier |
| 2005/0177241 A1 | 8/2005 | Angibaud et al. |
| 2005/0197708 A1 | 9/2005 | Stone et al. |
| 2005/0203536 A1 | 9/2005 | Laffargue et al. |
| 2005/0209700 A1 | 9/2005 | Rockwood et al. |
| 2005/0216092 A1 | 9/2005 | Marik et al. |
| 2005/0251263 A1 | 11/2005 | Forrer et al. |
| 2005/0256584 A1 | 11/2005 | Farrar |
| 2005/0267590 A1 | 12/2005 | Lee |
| 2005/0278030 A1 | 12/2005 | Tornier et al. |
| 2005/0278031 A1 | 12/2005 | Tornier et al. |
| 2005/0278032 A1 | 12/2005 | Tornier et al. |
| 2005/0278033 A1 | 12/2005 | Tornier et al. |
| 2005/0288681 A1 | 12/2005 | Klotz et al. |
| 2005/0288791 A1 | 12/2005 | Tornier et al. |
| 2006/0004462 A1 | 1/2006 | Gupta |
| 2006/0009852 A1 | 1/2006 | Winslow et al. |
| 2006/0015185 A1 | 1/2006 | Chambat et al. |
| 2006/0020344 A1 | 1/2006 | Schultz et al. |
| 2006/0030946 A1 | 2/2006 | Ball et al. |
| 2006/0173457 A1 | 8/2006 | Tornier |
| 2006/0235538 A1 | 10/2006 | Rochetin et al. |
| 2006/0241775 A1 | 10/2006 | Buss |
| 2007/0225817 A1 | 9/2007 | Reubelt et al. |
| 2007/0225818 A1 | 9/2007 | Reubelt et al. |
| 2007/0225821 A1 | 9/2007 | Reubelt et al. |
| 2007/0244564 A1 | 10/2007 | Ferrand et al. |
| 2007/0250174 A1 | 10/2007 | Tornier et al. |

FOREIGN PATENT DOCUMENTS

| | | |
|---|---|---|
| CH | 507704 | 5/1971 |
| DE | 19509037 | 9/1996 |
| DE | 19630298 | 1/1998 |
| EP | 0257359 | 8/1987 |
| EP | 0 299 889 A2 | 7/1988 |
| EP | 0524857 | 1/1993 |
| EP | 0549480 | 6/1993 |
| EP | 0599429 | 6/1994 |
| EP | 0617934 | 10/1994 |
| EP | 0664108 | 7/1995 |
| EP | 0679375 | 11/1995 |
| EP | 0712617 | 5/1996 |
| EP | 0715836 | 6/1996 |
| EP | 0797694 | 10/1997 |
| EP | 0807426 | 11/1997 |
| EP | 0809986 | 12/1997 |
| EP | 0864306 | 9/1998 |
| EP | 0903127 | 3/1999 |
| EP | 0903128 | 3/1999 |
| EP | 0927548 | 7/1999 |
| EP | 1062923 | 12/2000 |
| EP | 1064890 | 1/2001 |
| EP | 1195149 | 10/2002 |
| EP | 1 380 274 A1 | 1/2004 |
| EP | 1402854 | 3/2004 |
| FR | 2248820 | 10/1973 |
| FR | 2545352 | 11/1984 |
| FR | 2574283 | 6/1986 |
| FR | 2652498 | 4/1991 |
| FR | 2664809 | 1/1992 |
| FR | 2699400 | 6/1994 |
| FR | 2721200 | 12/1995 |
| FR | 2726994 | 5/1996 |
| FR | 2737107 | 1/1997 |
| FR | 2835425 | 8/2003 |
| FR | 2836039 | 8/2003 |
| SU | 749392 | 7/1980 |
| WO | WO 9107932 | 6/1991 |
| WO | WO 9309733 | 5/1993 |
| WO | WO 9617553 | 6/1996 |
| WO | WO 9846172 | 10/1998 |
| WO | WO 9949792 | 10/1999 |
| WO | WO 9965413 | 12/1999 |
| WO | WO 0015154 | 3/2000 |
| WO | WO 0041653 | 7/2000 |
| WO | WO 0147442 | 7/2001 |
| WO | WO 0239931 | 5/2002 |
| WO | WO 0239933 | 5/2002 |
| WO | WO 02067821 | 9/2002 |
| WO | WO 03005933 | 1/2003 |
| WO | WO 03/094806 | 11/2003 |
| WO | WO 2007/109291 | 9/2007 |
| WO | WO 2007/109319 | 9/2007 |
| WO | WO 2007/109340 | 9/2007 |

OTHER PUBLICATIONS

Rochetin et al., U.S. Appl. No. 11/401,415, entitled "Surgical Apparatus for Implantation of a Partial or Total," filed Apr. 11, 2006.

Rochetin, U.S. Appl. No. 11/670,274, entitled "Offset Stem Tibial Implantation," filed Feb. 1, 2007.

Ratron et al., U.S. Appl. No. 11/626,735, entitled "Surgical Instrumentation Kit for Inserting an Ankle Prothesis," filed Jan. 24, 2007.

John M. Fenlin Jr., M.D., Symposium on Surgery of the Shoulder, "Total Glenohumeral Joint Replacement," *Othopedic Clinics of North America*, vol. 6, No. 2, Apr. 1975, pp. 565-583.

Non-final Office Action for U.S. Appl. No. 11/165,287, mailed Aug. 3, 2007, 8 pp.

Response to non-final Office Action for U.S. Appl. No. 11/165,287, electronically transmitted on Nov. 12, 2007, 1 pg.

Final Office Action for U.S. Appl. No. 11/165,287, mailed Jan. 30, 2008, 12 pp.

Response to final Office Action for U.S. Appl. No. 11/165,287, electronically transmitted on Mar. 28, 2008, 1 pg.

Advisory Action for U.S. Appl. No. 11/165,287, mailed on Apr. 16, 2008, 3 pp.

Response to final Office Action and Advisory Action for U.S. Appl. No. 11/165,287, electronically transmitted on May 12, 2008, 1 pg.

Non-final Office Action for U.S. Appl. No. 11/165,287, mailed May 28, 2008, 9 pp.

Boileau et al., U.S. Appl. No. 12/020,913, entitled "Method and Apparatus for Fitting a Shoulder Prosthesis" filed Jan. 28, 2008.

"Aequalis-Fracture Suture Technique in 5 Steps," Tornier, Inc.

"Aequalis-Fracture Shoulder Prosthesis—Surgical Technique," Tornier, Inc.

"Aequalis® Press-Fit Shoulder Prosthesis—Surgical Technique," Tornier, Inc.

"Anatomical Shoulder™—Cemented Shoulder Prosthesis Product Information and Surgical Technique," Sulzer Medica, 2000.

"Anatomical Shoulder™ System Surgical Technique—Removable head option for improved surgical results," Zimmer, Inc., 2004.

Bigliani/Flatow®—The Complete Shoulder Solution, 4-Part Fracture of the Humerus Surgical Technique, Zimmer, Inc., 2000.

"Bio-Modular® / Bi-Polar Shoulder Arthroplasty," Biomet, Inc., 1997.

"Bio-Modular® Choice, Shoulder System," Biomet Orthopedics, Inc., 2004.

"Bio-Modular Total Shoulder Surgical Technique," Biomet Orthopedics, Inc., 2001.

"Copeland™ Humeral Resurfacing Head," Biomet Orthopedics, Inc., 2001.

"Global C.A.P.™ Surgical technique, resurfacing humeral head implant," DePuy International, Ltd., 2004.

Boileau, et al. "Adaptability and modularity of shoulder prosthese," *Maitrise Orthopédique*, https://www.maitriseorthop.com/corpusmaitri/orthopaedic/prothese_epaule_orthop/boileau_us.shtml, Jan. 3, 2006.

Boileau, et al. "Arthroscopic Repair of Full-Thickness Tears of the Supraspinatus: Does the tendon really heal?," *The Journal of Bone and Joint Surgery, Inc.*, pp. 1229-1240, 2005.

"Design Rationale," Latitude®.

Klein, Travis J., et al. "Mechanically favorable bone remodeling in rotator cuff arthropathy patients with good function," *Minneapolis Sports Medicine Center and University of Minnesota*.

Mansat, Michel, "Neer 3™, Surgical Technique for Fractrures," Smith & Nephew, 2000.

Molé, M.D., et al., "Aequalis-Reversed™ Shoulder Prosthesis, Surgical Technique," Tornier, Inc.

Nicholson, Gregory P., "Arthroplasty and Rotator Cuff Deficiency," Chapter 7, pp. 149-166.

"Offset Head, Bio-Modular® Total Shoulder," Biomet, Inc. 2000.

"The Foundation® Total Shoulder System," Encore Surgical.

"The Townley Modular Shoulder, Design by Reason," Biopro, Inc.

Zimmer® Bigliani/Flatow®—The Complete Shoulder Solution, Total Shoulder Arthroplasty Surgical Technique, Zimmer, Inc., 2003.

"Zimmer® Shoulder Retractors," Zimmer, Inc., 2000.

"Anatomic Glenold, Surgical Technique," Smith & Nephew, 2000.

"Anatomical Shoulder™ System—The new removable head option," Zimmer Inc., 2004.

"Delta CTA™ Reverse Shoulder Prosthesis," DePuy International, Ltd., 2004.

Cofield, M.D., Robert H. "Cofield$^2$ Total Shoulder System, Surgical Technique," Smith & Nephew, 1997.

"Aequalis®-Glenoid Keeled and Pegged—Surgical Technique," Tornier, Inc.

"Bigliani/Flatow®—The Complete Shoulder Solution, Designed by Shoulder Surgeons for Shoulder Surgery," Zimmer, Inc., 2001.

"Tornier Surgical Technique Addendum, Tornier Aequalis® Reversed Hemi-Adaptor Technique," Tornier, Inc., Aug. 8, 2005.

"Tornier Surgical Technique Addendum, Aequalis® Reversed Shoulder Polyethylene Insert," Tornier, Inc., Aug. 8, 2005.

Beuchel M.D., Frederick F. "Beuchel-Pappas™ Modular Salvage Shoulder System," Endotec, Inc., 2000.

Beuchel M.D., Frederick F. "Beuchel-Pappas™ Resurfacing Shoulder System," Endotec, Inc., 2000.

Beuchel M.D., Frederick F. "Beuchel-Pappas™ Total Shoulder System," Endotec, Inc., 2000.

Hertel M.D., PD, Ralph. "Technical considerations for implantation of EPOCA glenoid components (Leseprobe)," *Epoca Newsletter*, May 14, 2001.

Apoil, André "A Condyle for the Rotator Cuff Muscles, the total shoulder prosthesis," Aesculap®, 1994.

"Tornier Aequalis® Reversed 2 Prong Capsular Retractor," Tornier, Inc., Oct. 8, 2005.

"Tornier Aequalis® Reversed Shoulder G2 Baseplate," Tornier, Inc., Oct. 8, 2005.

* cited by examiner

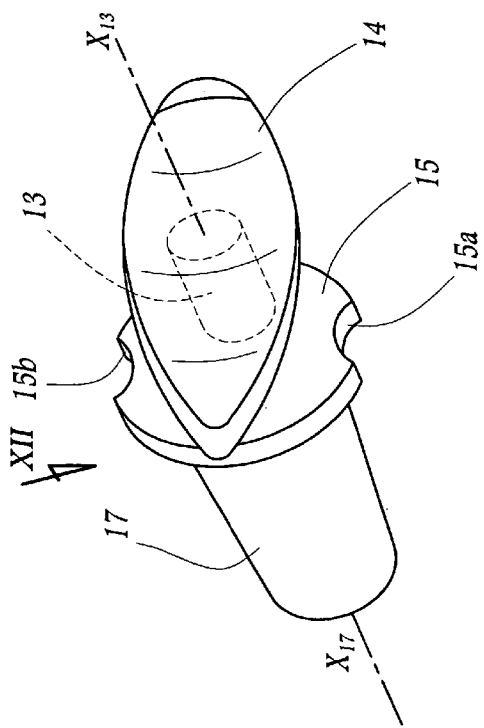
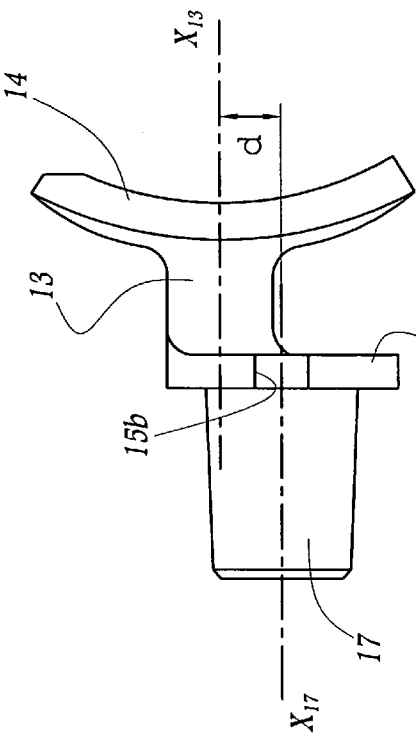
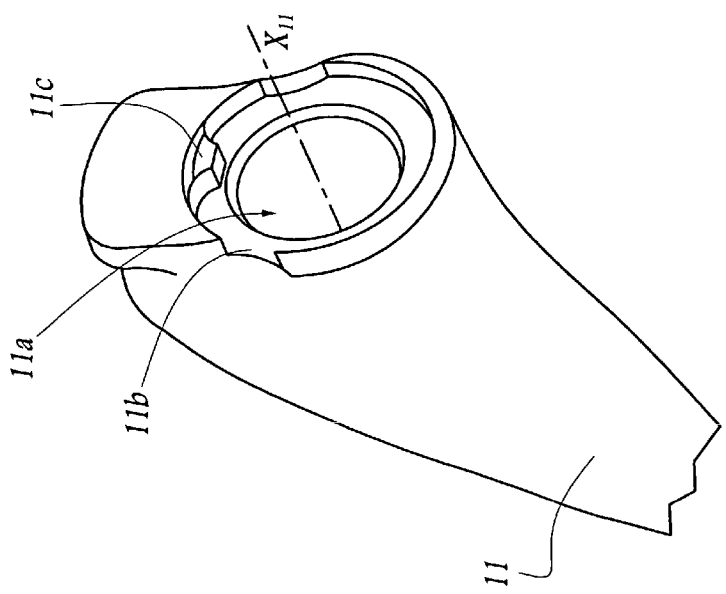
Fig.11
Fig.12

SHOULDER OR HIP PROSTHESIS AND PROCESS FOR FITTING SAME

FIELD OF THE INVENTION

The present invention relates to a complete or partial shoulder or hip prosthesis making it possible to reproduce, with an improved degree of precision, the characteristics of the natural joints. The invention also relates to a process for assembling such a prosthesis.

BACKGROUND OF THE INVENTION

In the domain of shoulder prostheses, it is known, for example from EP-A-0 299 889, to create a convex articular surface on a glenoid component, while a concave articular surface, of corresponding shape, is formed on a humeral component. The glenoid component of such a surface is very invasive and a subacromial conflict of the humeral component may occur at the end of the movement of abduction.

Furthermore, U.S. Pat. No. 4,846,840 discloses providing, on an intermediate element of a prosthesis, two substantially concentric convex surfaces with a view to their articulation on concave surfaces of corresponding shape, respectively provided on two bones which are to articulate on each other. Such a prosthesis is unstable insofar as no means is provided for avoiding that the two bones cooperating with the intermediate element, move apart from each other. In the event of failure of the articular ligaments, a dislocation cannot be excluded.

It is a more particular object of the invention to overcome these drawbacks by proposing a shoulder- or hip-joint prosthesis which reproduces the anatomical joint while facilitating the abduction of the arm or of the leg, in the absence of the rotator cuffs for the shoulder or of the stabilising structures of the hip.

SUMMARY OF THE INVENTION

In this spirit, the invention relates to a shoulder or hip prosthesis comprising a humeral or femoral component presenting a concave surface of articulation and an intermediate component presenting first and second convex surfaces of articulation intended to cooperate respectively with the concave surface of articulation of the humeral or femoral component and with a concave glenoid or acetabular surface of articulation which is natural or belongs to a glenoid or acetabular component. This prosthesis is characterized in that the concave surface of articulation of the humeral or femoral component is formed by a plate connected by a neck to a part of this component adapted to be anchored in the humeral or femoral medullary cavity, in that the intermediate component is provided with a member for retaining the humeral or femoral component in a position where the plate is in abutment against the first convex surface of the intermediate component, in that this retaining member defines a non-circular passage in which the aforementioned neck is adapted to be displaced, as a function of the movements of the humeral or femoral component with respect to the other components of the prosthesis, and in that this retaining member defines with the first convex surface of articulation of the intermediate component a volume for receiving a part of the plate which projects radially with respect to the neck.

Thanks to the invention, the retaining member contributes to the stability of the prosthesis, while the non-circular nature of the passage in which the neck is displaced makes it possible to envisage movements of abduction of great amplitude.

According to a first form of embodiment of the invention, the retaining member is substantially in the form of a U, with the result that the passage that it defines opens out on one side of this member.

According to other forms of embodiment of the invention, the retaining member may be in the form of a ring added on the intermediate component, with a central opening which constitutes the non-circular passage. This opening may be of substantially elliptical or substantially rectangular shape. The plate is in that case advantageously of non-circular cross section, particularly of substantially elliptical or rectangular shape.

The volume for reception defined between the retaining member and the first convex surface of articulation of the intermediate component may have a non-constant thickness about a median axis of the convex surface of the intermediate component which receives the plate in abutment. Similarly, it is possible that the thickness of that part of the plate which projects radially with respect to the neck is not constant about a central axis of this neck.

The retaining member may be removably mounted on a principal part of the intermediate component, particularly by means of an elastic blocking member, such as a circlip. In a variant, the retaining member may be in one piece with the intermediate component. According to another variant, it may be formed of a plurality of parts.

The humeral or femoral component may be in two parts, the part adapted to be anchored in the humeral or femoral medullary cavity defining a housing for receiving a stud fast with the neck and the plate. This stud may be centred on an axis offset with respect to a longitudinal axis of the neck. In that case, the housing may be provided to receive the stud in at least two positions in which the central axis of the stud is aligned with a central axis of the housing, the angular position of the longitudinal axis of the neck with respect to the central axis of the housing being, in that case, different in these positions.

The invention also relates to a process for mounting a prosthesis as described hereinabove and, more specifically, to a process which comprises steps consisting in:

introducing a stem belonging to the humeral or femoral component in a non-circular passage defined by a retaining member belonging to the intermediate component;

displacing an assembly, constituted by the stem, the aforementioned member and a plate which forms the concave surface of articulation of the humeral or femoral component, until this plate is in abutment against the first convex surface of articulation of the intermediate component, and immobilizing the aforementioned member with respect to a principal part of the intermediate component by retaining a part of the plate in this first convex surface.

In particular in the case of the retaining member being in one piece with the intermediate component, the process of assembly of the prosthesis comprises a step consisting in introducing the plate of the humeral or femoral component by force in the non-circular passage defined by the retaining member, with the result that its neck is engaged in this passage and a part of the plate is retained in a volume for reception defined between the retaining member and the first convex surface of the intermediate component.

The invention also relates to a method for fitting a shoulder or hip prosthesis, which comprises a process as mentioned hereinabove.

BRIEF DESCRIPTION OF THE DRAWINGS

The invention will be more readily understood and other advantages thereof will appear more clearly in the light of the following description of four forms of embodiment of a prosthesis in accordance with its principle, given solely by way of example and made with reference to the accompanying drawings, in which:

FIG. 11 is an exploded view in perspective of the humeral component of a shoulder prosthesis in accordance with a fourth form of embodiment of the invention, and FIG. 12 is a detailed view in the direction of arrow XII in FIG. 11.

DESCRIPTION OF PREFERRED EMBODIMENTS

Figure 1:
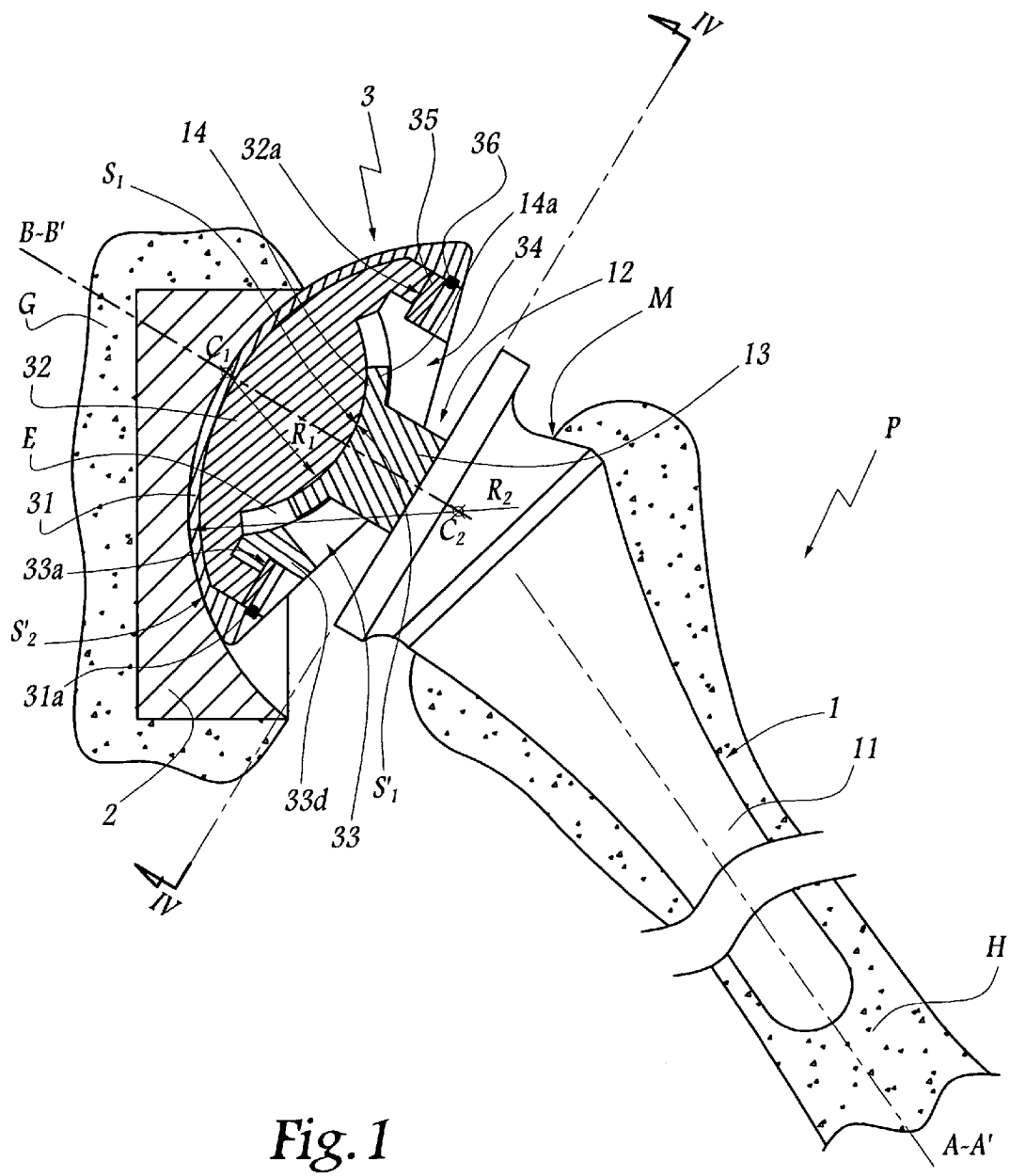
FIG. 1 is a sagittal section through a shoulder prosthesis according to the invention in place on a patient, while the patient's arm is in intermediate position.
Figure 2:
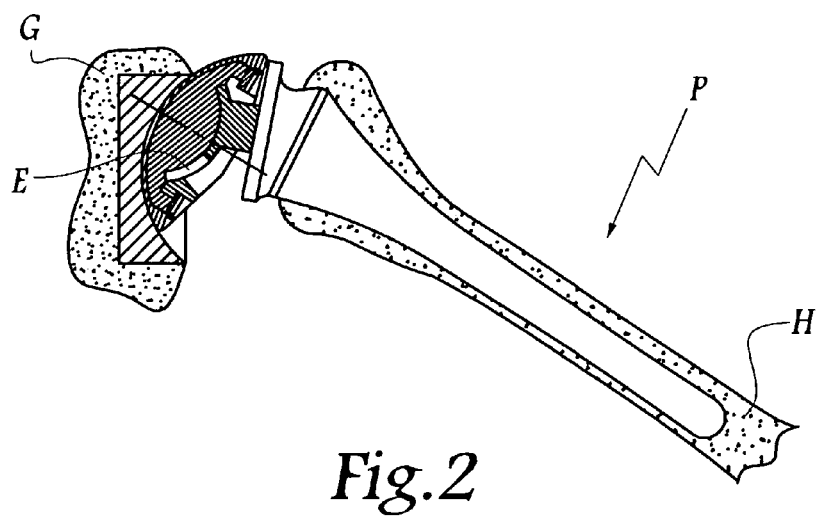
FIG. 2 is a section similar to FIG. 1, but on a smaller scale, while the patient's arm is in raised position with respect to that of FIG. 1.
Figure 3:
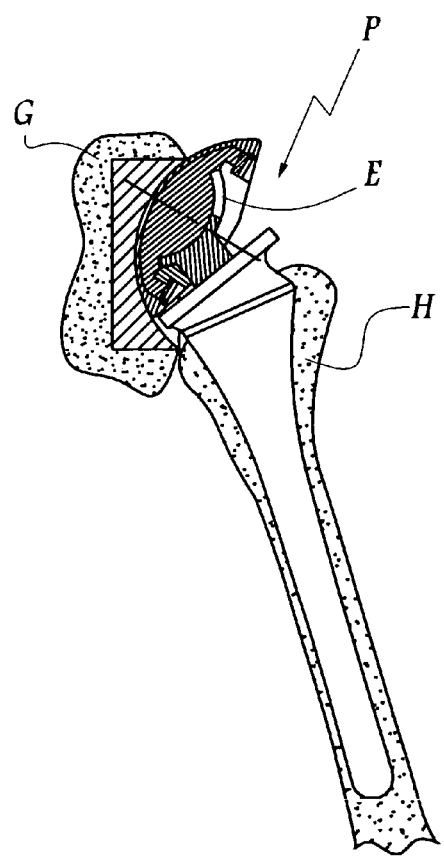
FIG. 3 is a section similar to FIG. 2, while the patient's arm is in lowered position.
Figure 5:
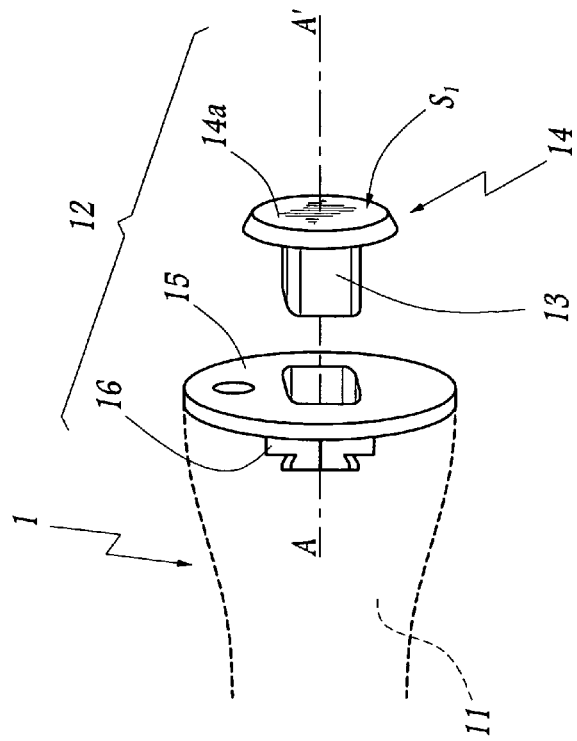
FIG. 5 is an exploded view in perspective of a part of the humeral component of the prosthesis of FIGS. 1 to 4.

Referring now to the drawings, the prosthesis P shown in FIGS. 1 to 5 comprises a humeral component 1 which includes a part 11 in the form of a stem intended to be anchored in the medullary cavity M of the humerus H of the joint to be fitted with the prosthesis P. A sub-assembly 12 is immobilized on part 11 by cooperation of shapes. This sub-assembly comprises a neck 13 in the form of a stem and a plate 14 which projects radially with respect to the neck about a central axis A-A' of the neck. The neck presents a substantially rectangular section, as may be seen in FIG. 4. The sub-assembly 12 also comprises a flange 15 on which the neck may be immobilized and which is provided with a dovetail 16 allowing it to be blocked on the part 11. Any other blocking means may be used here.

The neck 13 and the plate 14 are in one piece. They might equally well be formed by two distinct parts assembled together.

The plate 14 defines a concave surface $S_1$ whose concavity is turned towards the glenoid cavity G of the shoulder.

The prosthesis also comprises a glenoid component 2 anchored in the glenoid cavity G and defining a concave surface $S_2$ whose concavity is turned towards the outside of the glenoid cavity.

Figure 4:
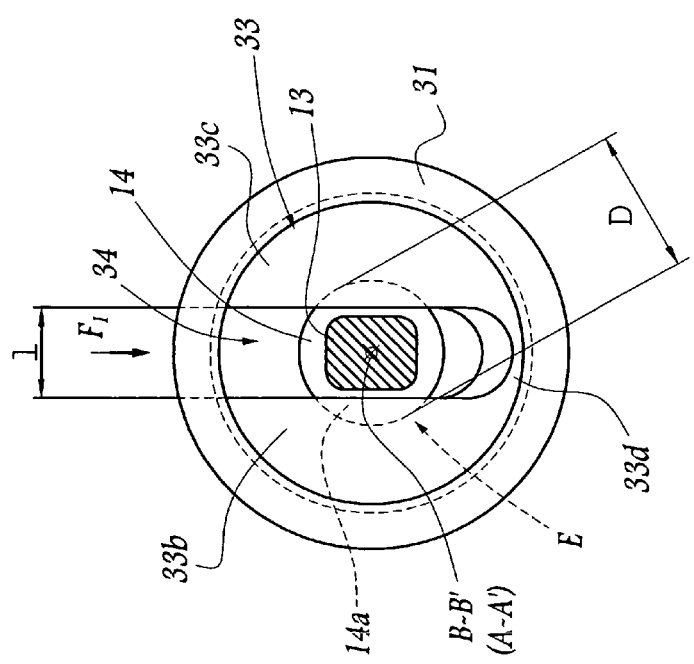
FIG. 4 is a section along line IV-IV in FIG. 1, the blocking washer, the circlip, the glenoid component and the glenoid cavity having been omitted in order to render the drawing clearer.

Between the components 1 and 2 there is interposed an intermediate component 3 comprising a hollow cup 31 inside which are immobilized a button or insert 32 and a substantially U-shaped member 33 as is visible in FIG. 4. 34 denotes the opening provided between the two branches of the member 33.

The elements 32 and 33 are maintained in position in the cup 31 by means of a washer 35 which comes into abutment against two annular surfaces 32a and 33a respectively provided on the insert 32 and on the member 33. This washer 35 is maintained in position with respect to the cup 31 by means of a circlip 36 engaged in an inner groove 31a of the cup 31.

$S'_1$ denotes the convex surface of the insert 32 accessible from outside the cup 31. The surfaces $S_1$ and $S'_1$ are both portions of a sphere and present substantially the same radius $R_1$, with the result that the plate 14 may slide over the surface $S'_1$ of the insert 32.

The convex outer surface $S'_2$ of the cup 31 is also in the form of a portion of a sphere, with a radius $R_2$ similar to the radius of the surface $S_2$, this allowing a relative sliding movement of the surfaces $S_2$ and $S'_2$.

In this way, the articulation of the humerus H with respect to the glenoid cavity G takes place by sliding of the surfaces $S_1$ and $S'_1$ on each other and of surfaces $S_2$ and $S'_2$ on each other.

The centre of rotation $C_1$ of the surfaces $S_1$ and $S'_1$ is located in the component 2, while the centre of rotation $C_2$ of the surfaces $S_2$ and $S'_2$ is located outside the prosthesis opposite the glenoid cavity.

In order to avoid detachment of the plate 14, the member 33 is provided to form a means for retaining the plate 14 in contact with the surface $S'_1$.

To that end, the branches 33b and 33c and the bottom 33d of the member 33 define with the surface $S'_1$ a space E in which may be engaged the part 14a of the plate 14 which projects, with respect to the neck 13, radially about axis A-A'. The width l of the opening 34 is less than the diameter D of the plate 14 which is circular. In this way, as soon as the neck 13 is in place in the opening 34, part 14a is engaged in the space E and the components 1 and 2 can no longer be moved away from each other as long as the member 33 is immobilized on the cup 31.

In FIG. 4, the washer 35 and the circlip 36 are not shown, this corresponding to an intermediate step of assembly of the prosthesis P in accordance with a first process.

In FIG. 4, the opening 34 opens out upwardly. However, the orientation of the member 33 may be chosen so that the opening 34 opens out in any direction in this Figure, as a function of the orientation of the movement of which it is desired to favour the amplitude.

For mounting the prosthesis, the member 33 is engaged on the neck 13 before the plate 14 is applied on the surface $S'_1$. This operation is easy, taking into account the U shape of the member 33, its branches 33b and 33c being, in that case, disposed on either side of the stem 13. The assembly formed by elements 13, 14 and 33 may then be displaced towards the insert 32 without being limited by the size of the opening 34 since the member 33 is in that case to the rear of the part 14a with respect to its direction of displacement. When the plate 14 is in contact with the insert 32, it then suffices to immobilize the member 33 on the cup 31 by means of the washer 35 and the circlip 36.

B-B' denotes the median axis of the surface $S'_1$ which merges with axis A-A' in the representation of FIG. 4. The fact that the opening 34 is not symmetrical about axis B-B' allows the plate 14, and consequently all the component 1, to be easily placed in position and efficiently retained with respect to the component 3.

Figure 6:
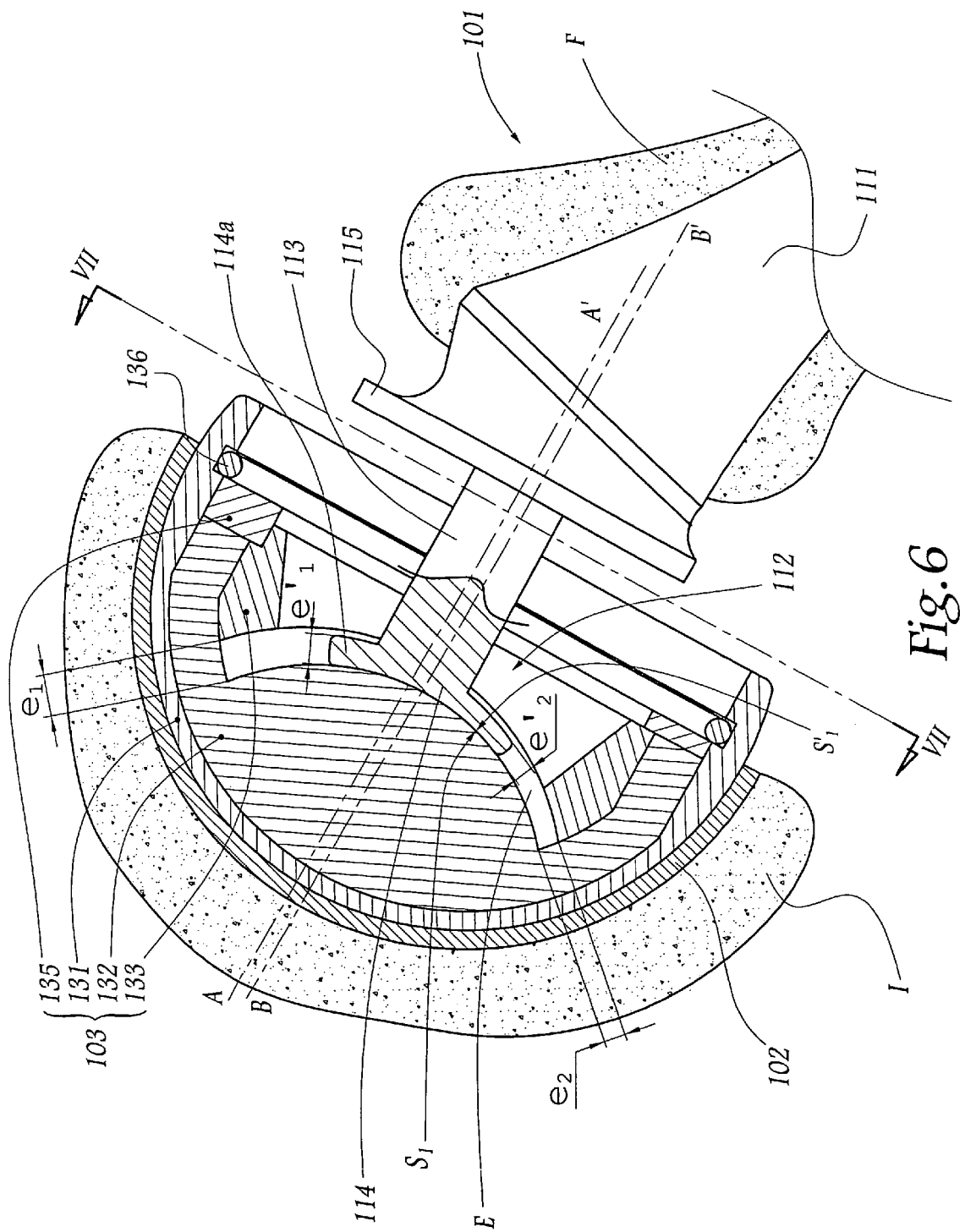
FIG. 6 is a partial sagittal section through a hip prosthesis in accordance with a second form of embodiment of the invention, while the patient's leg is in intermediate position.
Figure 7:
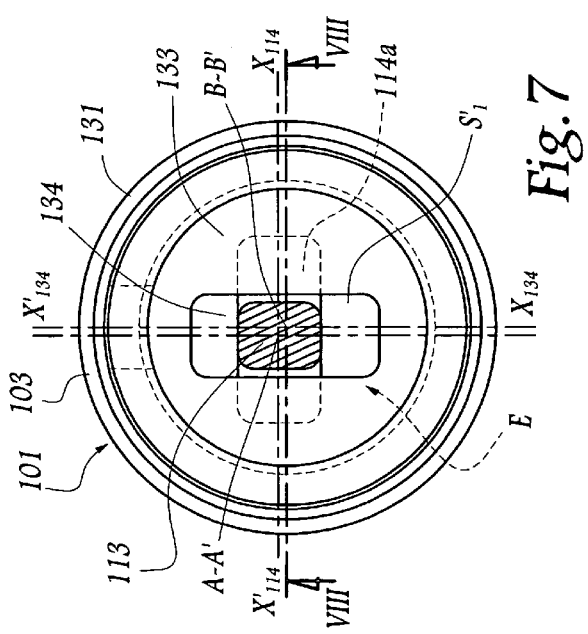
FIG. 7 is a section along line VII-VII in FIG. 6, the fixed component and the hip bone having been omitted in order to render the drawing clearer.

In the second embodiment shown in FIGS. 6 and 7, elements similar to those of the first embodiment bear identical references increased by 100. The intermediate component 103 of this embodiment comprises a cup 131 and an insert 132 which defines a surface $S'_1$ of articulation of a plate 114 belonging to a femoral component 101. The plate 114 is in one piece with a neck 113 with which it constitutes a sub-assembly 112 intended to be mounted on a part 111 anchored in the medullary cavity of the femur F. The fixed component 102 is anchored in the iliac bone I.

An annular ring 133 is mounted in the cup 131 as a member for retaining the plate 114. The central opening 134 of the ring 133 is substantially rectangular, with its major axis $X_{134}$-$X'_{134}$ substantially parallel to the sagittal plane.

The plate 114 is also substantially rectangular, with its major axis $X_{114}$-$X'_{114}$ oriented perpendicularly to the sagittal plane in the configuration of FIG. 7.

$S_1$ denotes the surface of articulation formed by the plate 114.

As previously, a space E is defined between the ring 133 and the insert 132 for receiving a part 114a of the insert 114 which projects radially with respect to the stem 113.

Figure 8:
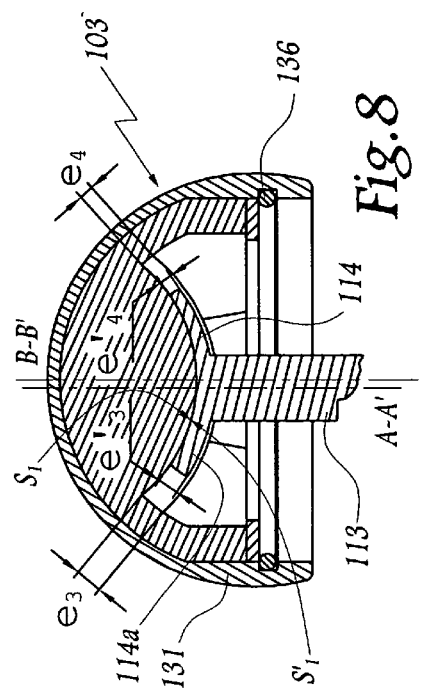
FIG. 8 is a section along line VIII-VIII in FIG. 7.

As is more particularly visible in FIGS. 6 and 8, the thickness $e_1$ of the space E in its upper part in FIG. 6 is greater than the corresponding thickness $e_2$ in the lower part. Similarly, the thickness $e_3$ of the space E to the left in FIG. 8 is greater than the corresponding thickness $e_4$ to the right in this Figure. In other words, the space E presents a non-constant thickness about the central median axis B-B' of the surface $S'_1$.

In addition, the part 114a of the plate 114 which projects radially with respect to the neck 113 likewise presents a non-constant thickness about axis A-A' of the neck 113, the thickness $e'_1$ of that portion of this part 114a intended to be introduced in the part of the space E of thickness $e_1$ being greater than that, $e'_2$, of the portion of the part 114a intended to be introduced in the part of the space E of thickness $e_2$. Similarly, that portion of the part 114a intended to be introduced in the part of the space E of thickness $e_3$ presents a thickness $e'_3$ greater than the thickness $e'_4$ of that portion of the part 114a intended to be introduced in the part of the space E of thickness $e_4$.

With this distribution of the respective thicknesses of the space E and of the part 114a of the plate 114, control of the angular position of the neck 113 and consequently of the whole of the component 1 about the central axis A-A' of the neck 113, is obtained.

Such control avoids the plate 114 tending to return into a configuration where it might be torn through the opening 134 of the ring 133.

Mounting of the prosthesis P of this embodiment takes place by disconnecting the neck 113 from the flange 115 of the sub-assembly 112. This makes it possible to introduce the neck 113 in the opening 134 then to connect the neck 113 and the flange 115 again by any appropriate means. It is then possible to apply the plate 114 against the insert 132 by bringing the ring 133 into contact with the insert 132 and the cup 131. This ring may in that case be immobilized with respect to the elements 131 and 132 by placing a bearing washer 135 and a circlip 136 in position.

When the ring 133 is brought into contact with the insert 132, the plate 114 is oriented such that its largest dimension is substantially perpendicular to the largest dimensions of the opening 134, care being taken that the zones of thickness $e'_1$, $e'_2$, $e'_3$ and $e'_4$ be respectively caused to merge with the parts of the member 133 intended to define the zones of the space E of thicknesses $e_1$, $e_2$, $e_3$ and $e_4$. In this way, once the ring 133 is applied on the component 103, the plate 114 is necessarily oriented in the configuration of FIGS. 6 to 8 and does not risk accidentally returning towards a configuration where it might be extracted through the opening 134, particularly in the case of its dimensions being smaller than those of the opening.

As in the first embodiment, the plate 114 is retained in abutment on the surface $S'_1$ during the whole movement of abduction, including in central position corresponding to that of FIG. 1.

Figure 9:
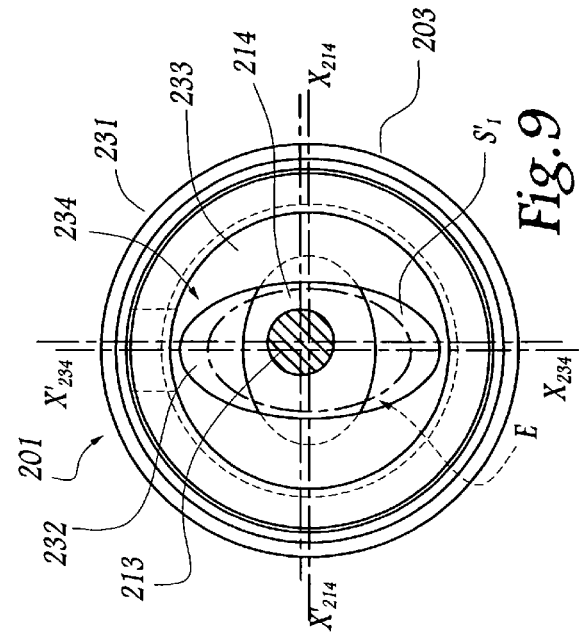
FIG. 9 is a section similar to FIG. 7 for a shoulder prosthesis in accordance with a third form of embodiment of the invention.
Figure 10:
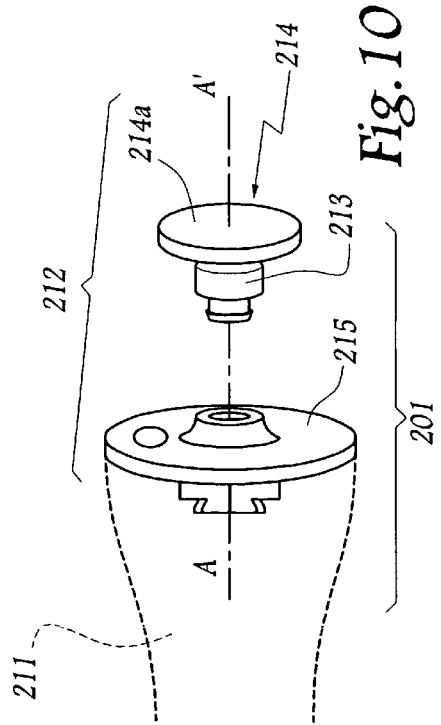
FIG. 10 is an exploded view in perspective of a part of the humeral component of the prosthesis of FIG. 9.

In the third embodiment of the invention shown in FIGS. 9 and 10, elements similar to those of the first embodiment bear identical references increased by 200. This embodiment concerns a shoulder prosthesis whose intermediate component 203 comprises a cup 231 and a ring 233 whose central opening 234 is of substantially elliptical shape, with its longitudinal axis $X_{234}$-$X'_{234}$ substantially parallel to the sagittal plane.

The sub-assembly 212 of the humeral component 201, which forms a surface of articulation $S_1$ adapted to cooperate with the surface of articular $S'_1$, defined by the insert 232 of the component 203, is more particularly visible in FIG. 9. Its plate 214 is of substantially elliptical shape, its neck 213 being circular. The neck 213 is adapted to be immobilized on a flange 215 from which it may be separated, as will appear from the following explanations.

214a denotes that part of the plate 214 which projects radially with respect to the neck 213. As previously, the part 214a of the plate 214 presents a non-constant thickness about axis A-A' of the neck 213, while the space E defined between the elements 233 and 232 to receive this part likewise presents a non-constant thickness. For example, that part of the space E shown to the left in FIG. 10 may have a relatively small thickness, like the corresponding section of the part 214a, while the space E presents a greater thickness to the right in FIG. 10, like the corresponding section of the part 214a. This difference in thickness contributes to maintaining the plate 214 in position with respect to the component 203 in rotation about axis B-B'.

Assembly of the prosthesis in accordance with this embodiment takes place similarly to the assembly of the second embodiment. The neck 213 is disconnected from the flange 215 and this neck 213 is introduced in the opening 234 of the washer 233. The plate 214 is then applied against the surface $S'_1$ of the intermediate component by respecting an orientation compatible with the different thicknesses of the part 214a and of the space E, this making it possible to bring the washer 233 into contact with the cup 231 and to immobilize it by any appropriate means, particularly a washer of the type of washer 135 of the second embodiment.

The neck 213 and the flange 215 may be connected before or after the plate 214 is applied against the surface $S'_1$. This also applies to the second embodiment.

According to a variant of the invention (not shown), the flange 215 and the part 211 intended to be anchored in the medullary cavity are in one piece. According to another variant, the neck 213 is introduced directly in a housing formed by the part 211.

In the fourth embodiment of the invention shown in FIG. 11, elements similar to those of the first embodiment bear identical references. The medullary stem 11 defines a truncated housing 11a centred on an axis $X_{11}$ and bordered by a substantially annular bearing surface 11b. The plate 14 and the neck 13 are in one piece with the flange 15 and with a stud 17 intended to be introduced in the housing 11a and immobilized therein by cooperation of shapes. The assembly formed by elements 13, 14, 15 and 17 is visible in the plan view in FIG. 12. The outer surface of the stud 17 is truncated with the same angle of conicity as the surface defining the housing 11a.

$X_{17}$ denotes the central axis of the stud 17. Axes $X_{11}$ and $X_{17}$ merge when the stud 17 is received in the housing 11a. $X_{13}$ denotes the central axis of the neck 13. Axis $X_{13}$ is offset radially with respect to axis $X_{17}$ by a non-zero distance d, this making it possible to adjust the position of the plate 14 with respect to the intermediate component (not shown) of this embodiment.

The flange 15 is intended to come into abutment on the surface 11b and is provided with two notches 15a and 15b intended to be disposed at the level of a projection 11c formed above the annular surface 11b with the result that the assembly formed by elements 13, 14, 15 and 17 may be mounted on part 11 in two positions, depending on whether the projection 11c is received in the notch 15a or in the notch 15b. Two possible positions are thus obtained for the plate 14 with respect to the part 11, by reason of the two angular positions obtained for axis $X_{13}$ with respect to axes $X_{11}$ and $X_{17}$.

According to a variant of the invention (not shown), axes $X_{17}$ and $X_{13}$ may be aligned.

The foregoing description has mentioned the positioning of the plate with respect to the intermediate component; this is a relative positioning and the assembling may be effected by maintaining the humeral or femoral plate immobile and by displacing the intermediate component.

The invention has been represented with retaining members 33, 133 or 233 added on the intermediate component 3, 103 or 203. However, it is applicable with a retaining member in one piece with the intermediate component. In that case, the plate is introduced by force through the passage of the retaining member while the prosthesis is being mounted, this making it possible to engage the corresponding neck in this passage. Such a force-fit may also be envisaged with the prostheses of the embodiments shown.

According to another variant of the invention (not shown), the retaining member may be in two or even more parts.

Independently of the embodiment considered, the intermediate component may be made entirely of synthetic material, particularly of polyethylene, or entirely of ceramics. However, this is not obligatory, as may be seen from the Figures.

It will be understood that the processes of mounting mentioned hereinabove may form part of a method for fitting a prosthesis in accordance with the invention, the stem 11, 111 or equivalent of the humeral or femoral component being firstly anchored in the corresponding medullary cavity, assembling with the intermediate component being effected thereafter.

The invention has been shown when implemented with complete shoulder and hip prostheses. However, it is applicable with a shoulder prosthesis without glenoid component, the concave surface of the glenoid cavity being used instead of the surface $S_2$ shown in the Figures. The same applies in the case of a hip prosthesis where the natural acetabular cavity may be used.

The characteristics of the different embodiments shown may be combined together within the framework of the present invention. In particular, the prosthesis of the second embodiment may be adapted to the shoulder, while the prostheses of the first and third embodiments may be adapted to the hip.

What is claimed is:

1. A shoulder or hip prosthesis comprising:
    a first component having a concave surface of articulation formed by a plate, wherein the plate is connected to a first end of the first component by a neck, wherein the first end of the first component is adapted to be anchored in a medullary cavity;
    a second component having a concave surface of articulation; and
    an intermediate component having a first convex surface of articulation and a second convex surface of articulation, wherein the first and second convex surfaces of articulation cooperate respectively with the concave surface of articulation of the first component and with the concave surface of articulation of the second component, and wherein the second convex surface of articulation of the intermediate component is unconstrained relative to the concave surface of articulation of the second component;
    wherein the intermediate component has a retaining member for retaining the concave surface of articulation of the first component in abutment against the first convex surface of the intermediate component;
    wherein the retaining member has a non-circular passage in which the neck of the first component is adapted to be displaced as a function of movements of the first component with respect to the second and intermediate components; and
    wherein the retaining member and the first convex surface of articulation of the intermediate component define a volume for receiving a second end of the plate which projects radially with respect to the neck.

2. The prosthesis of claim 1, wherein the retaining member is substantially in the form of a U.

3. The prosthesis of claim 1, wherein the retaining member is in the form of a ring having a central opening, wherein the ring is connectable to the intermediate component, and wherein the central opening of the ring forms the non-circular passage.

4. The prosthesis of claim 3, wherein the central opening is of substantially rectangular shape.

5. The prosthesis of claim 3, wherein the central opening is of substantially elliptical shape.

6. The prosthesis of claim 1, wherein the plate has a non-circular cross section, particularly of substantially elliptical or rectangular shape.

7. The prosthesis of claim 1, wherein the volume for receiving the second end of the first component has variable thickness about a central median axis of the first convex surface of articulation.

8. The prosthesis of claim 1, wherein the second end of the plate has variable thickness about a central axis of the neck.

9. The prosthesis of claim 1, wherein the retaining member is removably mounted on the intermediate component by means of an elastic blocking member.

10. The prosthesis of claim 1, wherein the retaining member is integral with the intermediate component.

11. The prosthesis of claim 1, wherein the retaining member is formed by at least two parts.

12. The prosthesis of claim 1, wherein the first component has a first part and a second part, wherein the first part is adapted to be anchored in the medullary cavity and wherein the first part defines a housing for receiving a stud connected to the neck and the plate.

13. The prosthesis of claim 12, wherein a central axis of the stud is offset with respect to a longitudinal axis of the neck.

14. The prosthesis of claim 13, wherein the housing is adapted to receive the stud in at least two positions in which the central axis of the stud is aligned with a central axis of the housing, and wherein an angular position of the longitudinal axis of the neck is different in the two positions with respect to the central axis of the housing.

15. A shoulder or hip prosthesis comprising:
a first component comprising:
    a neck; and
    a plate connected to the neck, wherein the plate forms a concave surface of articulation;
a second, intermediate component comprising:
    a first convex surface of articulation;
    a second convex surface of articulation; and
    a retaining member for retaining the first component in abutment against the first convex surface of the second component, wherein the retaining member and the first convex surface of the second component define a volume for receiving a projection extending radially from the plate with respect to the neck; and
a third component comprising a concave surface of articulation;
wherein the first and second convex surfaces of articulation cooperate respectively with the concave surface of articulation of the first component and the concave surface of articulation of the second component, wherein the second convex surface of articulation of the second component is unconstrained relative to the concave surface of articulation of the third component, and wherein the retaining member defines a non-circular passage in which the neck is adapted to be displaced as a function of movement of the first component with respect to the second and third components.

16. A shoulder or hip prosthesis comprising:
a first component comprising:
    a plate forming a concave surface of articulation;
    a stem anchored in a medullary cavity; and
    a neck connecting the plate to the stem;
a second component comprising:
    a retaining member having a non-circular passage for maintaining the first component against the second component;
    a first convex surface of articulation; and
    a second convex surface of articulation;
    wherein the neck of the first component is displaced within the non-circular passage of the retaining member; and
    wherein the retaining member and the first convex surface of articulation define a volume for receiving a radially extending part of the plate with respect to the neck; and
a third component having a concave surface of articulation;
wherein the first convex surface of articulation engages the concave surface of articulation of the first component and the second convex surface of articulation engages the concave surface of articulation of the third component; and
wherein the second convex surface of articulation of the second component is unconstrained relative to the concave surface of articulation of the third component.

* * * * *